US00PP31937P2

(12) United States Plant Patent
van Geest

(10) Patent No.: US PP31,937 P2
(45) Date of Patent: Jul. 7, 2020

(54) ***FICUS* PLANT NAMED 'ESPE1803'**

(50) Latin Name: *Ficus auriculata*
Varietal Denomination: ESPE1803

(71) Applicant: J. Van Geest Holding B.V., Gravenzande (NL)

(72) Inventor: Jan van Geest, Gravenzande (NL)

(73) Assignee: J. Van Geest Holding B.V., Gravenzande (NL)

( * ) Notice: Subject to any disclaimer, the term of this patent is extended or adjusted under 35 U.S.C. 154(b) by 0 days.

(21) Appl. No.: 16/501,277

(22) Filed: Mar. 16, 2019

(51) Int. Cl.
*A01H 5/00* (2018.01)
*A01H 6/00* (2018.01)

(52) U.S. Cl.
USPC ..... Plt./211

(58) Field of Classification Search
USPC ..... Plt./211
CPC ... A01H 5/00; A01H 5/08; A01H 5/12; A01H 6/00
See application file for complete search history.

(56) References Cited

PUBLICATIONS

Clemson Cooperative Extension Home & Garden Information Center Weeping Ficus 2016 [retrieved on Nov. 19, 2019] [online] retrieved from Internet at https://hgic.clemson.edu/factsheet/weeping-ficus/, 4 pp. (Year: 2016).*

* cited by examiner

*Primary Examiner* — June Hwu
(74) *Attorney, Agent, or Firm* — Samuel R. McCoy, Jr.

(57) ABSTRACT

A new and distinct variety of *Ficus* plant named 'ESPE1803' which is characterized by the combination of large bullate foliage with conspicuous light yellow-green venation, and the stability of all characteristics from generation to generation.

3 Drawing Sheets

Latin name of the genus and species: The Latin name of the genus and species of the novel variety disclosed herein is *Ficus auriculata.*

Variety denomination: The inventive variety of *Ficus* disclosed herein has been given the variety denomination 'ESPE1803'.

BACKGROUND OF THE INVENTION

Parentage: 'ESPE1803' originated as a naturally occurring, whole-plant mutation of an unnamed and unpatented *Ficus auriculata* plant. In the summer of 2015, the inventor discovered the mutation at his commercial greenhouse in Gravenzande, The Netherlands, growing amongst a cultivated population of unnamed and unpatented *Ficus auriculata* plant which exhibit a small, compact plant size. The mutation was noted for its large bullate foliage and was subsequently isolated for further evaluation in order to confirm the distinctness and stability of the characteristics first observed. Upon confirmation of distinctness and stability, 'ESPE1803' was selected for commercialization.

Asexual Reproduction: Asexual reproduction of 'ESPE1803', by way of stem cuttings, was first initiated in the summer of 2015 at a commercial greenhouse in Gravenzande, The Netherlands. Through five subsequent generations, the unique features of this cultivar have proven to be stable and true to type.

SUMMARY OF THE INVENTION

The cultivar 'ESPE1803' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'ESPE1803'. These characteristics in combination distinguish 'ESPE1803' as a new and distinct *Ficus* cultivar:

1. *Ficus* 'ESPE1803' exhibits large foliage, relative to the plant height; and
2. *Ficus* 'ESPE1803' exhibits bullate foliage with conspicuous venation; and
3. *Ficus* 'ESPE1803' exhibits green foliage with very light yellow-green venation; and
4. *Ficus* 'ESPE1803' exhibits foliage which is held upright.

BOTANICAL DESCRIPTION OF THE PLANT

Figure 1:
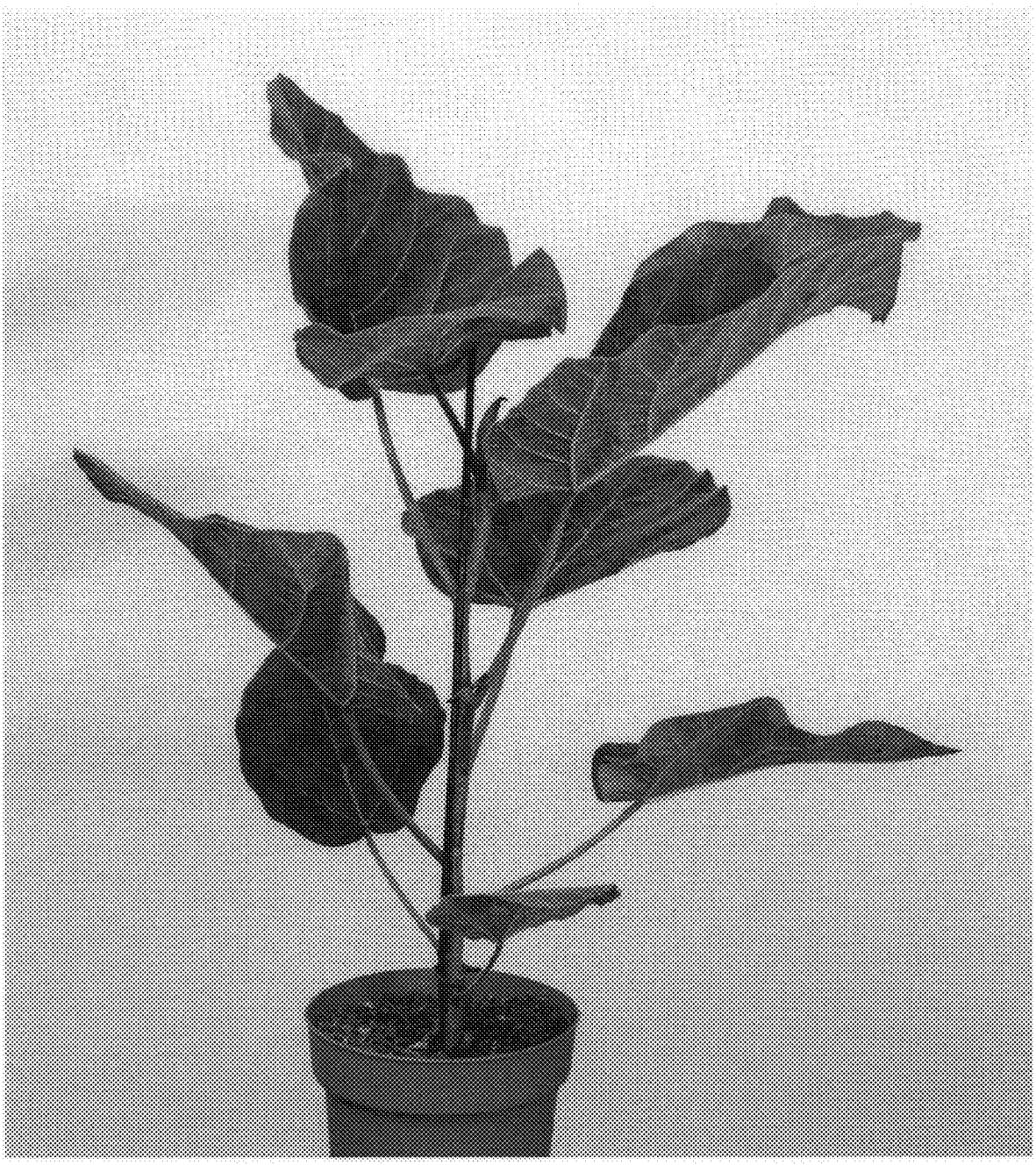
FIG. 1 illustrates, as nearly true as it is reasonably possible to make the same in color photographs of this type, an exemplary plant of 'ESPE1803' grown in a commercial greenhouse in Gravenzande, The Netherlands. This plant is approximately 26 weeks old, shown planted in a 15 cm container.
Figure 2:
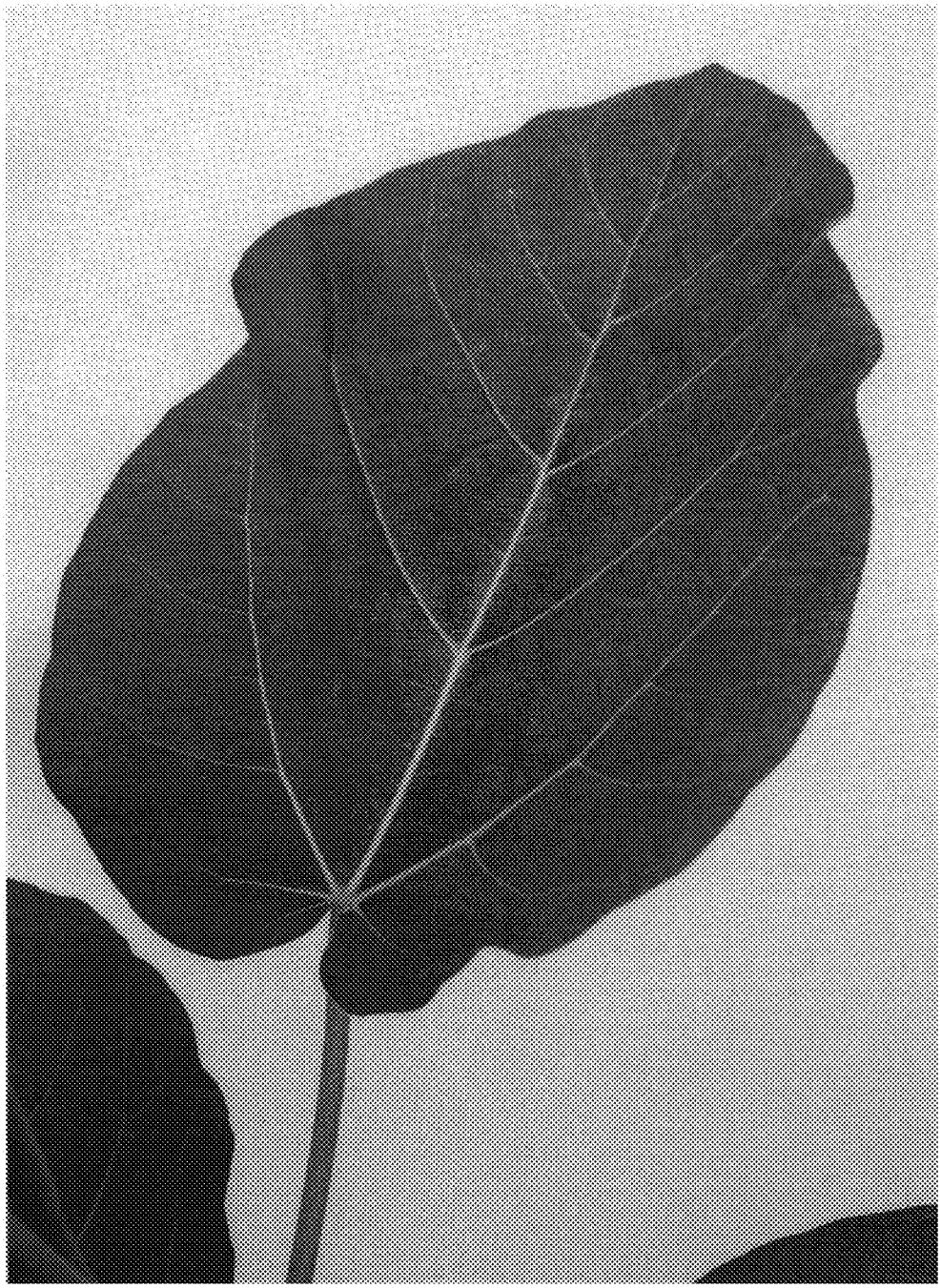
FIG. 2 illustrates, as nearly true as it is reasonably possible to make the same in color photographs of this type, the adaxial surface of the mature foliage of 'ESPE1803'.
Figure 3:
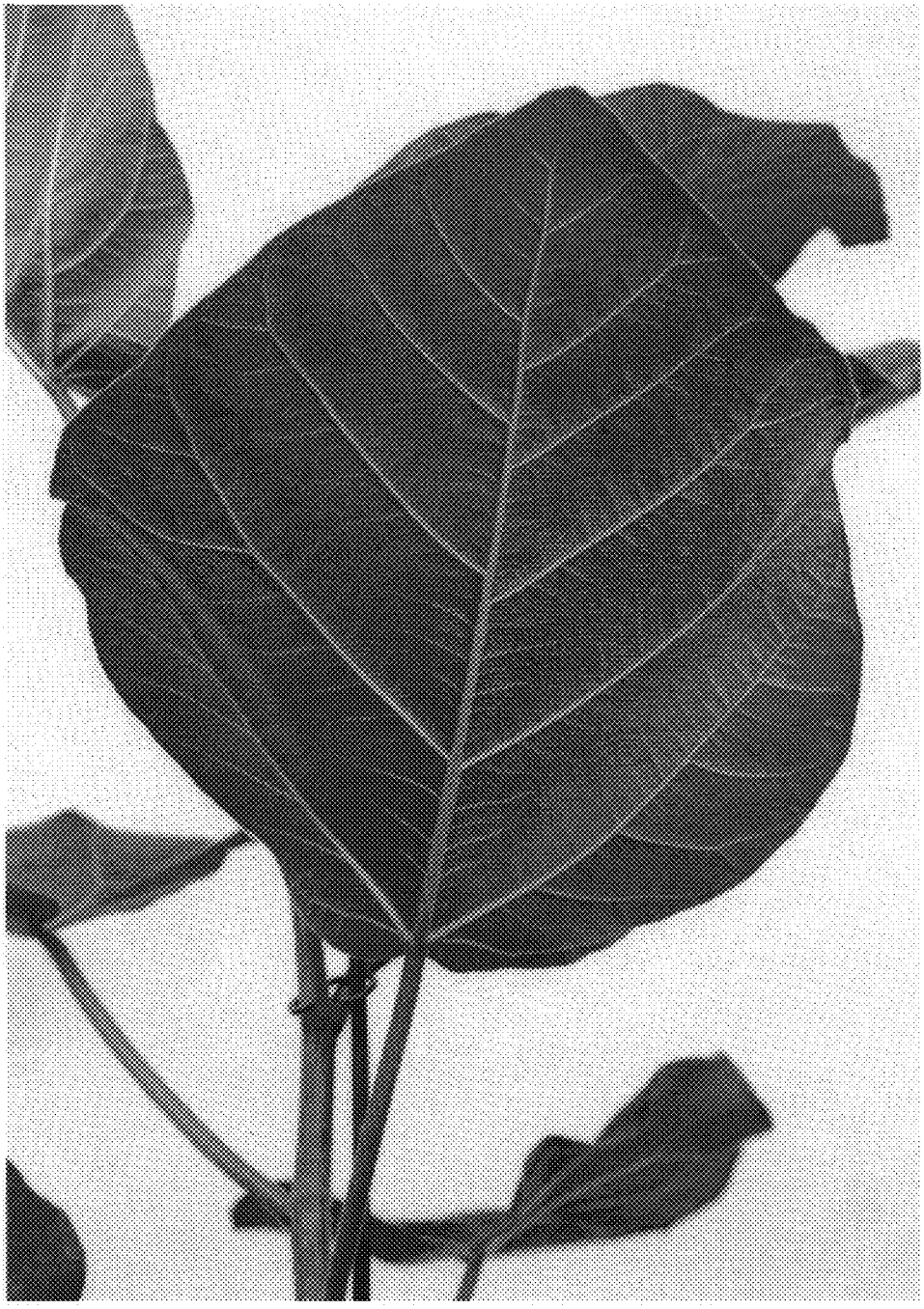
FIG. 3 illustrates, as nearly true as it is reasonably possible to make the same in color photographs of this type, the adaxial surface of the mature foliage of 'ESPE1803'.

The following observations and measurements were made in February of 2019 and describe a sample set of six 26 week-old 'ESPE1803' plants grown in 15 cm nursery pots at a greenhouse in Gravenzande, The Netherlands. Plants were produced in a greenhouse with full sun exposure, ebb and flood irrigation tables, no supplemental fertilizer, and no preventative or pest control measures utilized.

Those skilled in the art will appreciate that certain characteristics will vary with older or, conversely, with younger plants. 'ESPE1803' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'ESPE1803' and comparisons with the parent plant and most similar commercial variety of *Ficus* are provided below.

Plant description:

*Growth habit*.—Upright.

*Plant form*.—Broad obovate.

*Average height*.—70.5 cm from the soil level to the top of the foliar plane.

*Plant spread*.—Average of 80.0 cm.

*Growth rate*.—Moderately fast.

*Plant vigor*.—Moderately vigorous.

*Propagation type*.—Stem cuttings and meristematic tissue culture propagation.

*Time to produce a rooted cutting*.—Approximately 15 weeks to produce a rooted cutting at approximately 25 degrees Celsius.

*Time to produce a finished plant*.—Approximately 15 weeks to produce a marketable finished plant in a 14 cm pot.

*Disease resistance*.—Neither resistance nor susceptibility to typical *Ficus auriculata* pests and diseases has been observed.

*Environmental tolerances*.—Adapt to, at least, USDA Zones 10 through 13 and temperatures as high as 40 degrees Celsius; moderate to high tolerance to rain; low to moderate tolerance to wind.

Root system:

*General*.—Moderately dense, moderately branched rooting; roots are slightly fibrous.

*Distribution in the soil profile*.—Moderately deep.

*Diameter of roots*.—1.0 mm on average.

*Texture*.—Smooth; no root hairs.

*Color*.—Greyed-orange, nearest to a mixture of RHS 163B and 163C.

Stem:

*General branching habit*.—Basally branching main stems; no lateral branching. Pinching isn't required but will improve branching.

*Quantity of stems*.—1.

*Length*.—Approximately 50.0 cm.

*Diameter*.—Approximately 1.1 cm.

*Internode length*.—Approximately 6.7 cm.

*Attitude*.—Near vertical. Shoot tips are semi-erect.

*Aspect*.—Rounded; very angular.

*Texture*.—Densely covered with short hairs, with an average length of 1.0 mm. Hairs are colored greyed-brown, nearest to RHS 199D.

*Luster*.—Matte.

*Strength*.—Strong.

*Color, juvenile*.—Greyed-brown, nearest to RHS 199A.

*Color, mature*.—Yellow-green, nearest to a combination of RHS 146A and 146B.

*Color at internodes*.—Yellow-green, nearest to a combination of RHS 146A and 146B.

*Color of the oldest wood*.—Yellow-green, nearest to RHS 148A, and axially striped greyed-brown, nearest to a combination of RHS 199A and 199B.

Foliage:

*Arrangement*.—Alternate.

*Division*.—Simple.

*Quantity*.—8 leaves, as observed along the main stem.

*Attitude*.—At an average angle of 45 degrees to the stem.

*Lamina*.—Shape — Cordate. Aspect — Slightly carinate and varying from concave to convex to flat on individual leaves. Dimensions — 32.4 cm long and 18.0 cm wide. Apex — Abruptly acute. Base — Cordate. Margin — Entire; coarsely undulate. Texture of adaxial surface — Slightly bullate and densely covered with very short hairs, with an average length of 0.75 mm long. Hairs are colored green-white, nearest to RHS 157D. Texture of abaxial surface — Slightly bullate and densely covered with very short hairs, with an average length of 1.0 mm long. Hairs are colored green-white, nearest to RHS 157D. Luster of the adaxial surface — Very slightly glossy. Luster of the abaxial surface — Very slightly glossy. Color — Juvenile foliage, adaxial surface — Green, nearest to RHS 137A, and veined yellow-green, nearest to RHS 154C. Juvenile foliage, abaxial surface — Yellow-green, nearest to RHS 147B, and veined lighter, nearest to RHS 154C. Mature foliage, adaxial surface — Nearest to in between green and yellow-green, RHS NN137A and 147A. Mature foliage, abaxial surface — Nearest to in between yellow-green and greyed-green, RHS 147B and 191A. Venation — Pattern — Pinnate. Color, adaxial surface — Yellow-green, nearest to RHS 145B. Color, abaxial surface — Yellow-green, nearest to RHS 150D.

*Stipule*.—Not present.

*Petiole*.—Length — 17.4 cm. Diameter — 0.8 cm. Strength — Strong. Texture — Densely covered with short thin hairs, approximately 1.0 mm long. Hairs are colored greyed-orange, nearest to RHS 164D. Luster — Very slightly glossy. Color, adaxial surface — Yellow-green, nearest to RHS 146D. Color, abaxial surface — Yellow-green, nearest to in between RHS 146D and 151A.

Inflorescence: No flowering has been observed to date.

COMPARISON WITH THE PARENT PLANT

Plants of the new cultivar 'ESPE1803' differ from the parent, an unnamed and unpatented *Ficus auriculata* plant, in the following characteristics described in Table 1 below.

TABLE 1

| Characteristic | 'ESPE1803' | The parent. |
|---|---|---|
| Foliage abundance. | Less abundant. | More abundant. |
| Foliage size. | Larger than the parent. | Smaller than 'ESPE1803' |

TABLE 1-continued

| Characteristic | 'ESPE1803' | The parent. |
|---|---|---|
| Foliage luster. | Very slightly glossy. | Glossy. |
| General coloration of the mature foliage. | Darker green. | Lighter green. |

COMPARISON WITH THE CLOSEST KNOWN COMPARATOR

Plants of the new cultivar 'ESPE1803' differs from the variety, *Ficus bussei* 'ESFIBU1802' (U.S. patent application Ser. No. 16/501,282), for which a United States plant patent application is being filed concurrently with the instant application, in the following characteristics described in Table 2 below.

TABLE 2

| Characteristic | 'ESPE1803' | 'ESFIBU1802' |
|---|---|---|
| Foliage shape. | Cordate. | Ovate. |
| General coloration of the foliage. | Darker green. | Lighter green. |
| General coloration of the foliage venation. | Very light yellow-green. | Green. |
| General coloration of the stems. | Yellow-green. | Green. |

That which is claimed is:

1. A new and distinct variety of *Ficus* plant named 'ESPE1803', substantially as described and illustrated herein.

* * * * *